United States Patent [19]

Flitter et al.

[11] Patent Number: 5,955,506
[45] Date of Patent: *Sep. 21, 1999

[54] BENZAMIDES FOR NEURODEGENERATIVE DISORDER TREATMENT

[75] Inventors: William David Flitter, Mountain View; William A. Garland, San Mateo; Allan L. Wilcox, Fremont, all of Calif.; Richard E. Paylor, Bethesda, Md.

[73] Assignee: Centaur Pharmaceuticals, Inc., Sunnyvale, Calif.

[*] Notice: This patent is subject to a terminal disclaimer.

[21] Appl. No.: 08/930,286

[22] PCT Filed: Apr. 3, 1996

[86] PCT No.: PCT/US96/04538

§ 371 Date: Feb. 2, 1998

§ 102(e) Date: Feb. 2, 1998

[87] PCT Pub. No.: WO96/31462

PCT Pub. Date: Oct. 10, 1996

[51] Int. Cl.$^6$ ............... A61K 31/165; C07C 233/05
[52] U.S. Cl. ............... 514/616; 564/153; 564/155
[58] Field of Search ............ 514/616; 564/153, 564/155, 142

[56] References Cited

U.S. PATENT DOCUMENTS

| | | | |
|---|---|---|---|
| 4,044,147 | 8/1977 | Nelson | 424/309 |
| 4,927,928 | 5/1990 | Shroot et al. | 544/154 |
| 5,212,203 | 5/1993 | Shroot et al. | 514/617 |
| 5,280,044 | 1/1994 | Crowley et al. | 514/616 |
| 5,346,691 | 9/1994 | Raspanti et al. | 424/59 |
| 5,472,983 | 12/1995 | Flitter et al. | 514/599 |
| 5,658,953 | 8/1997 | Flitter et al. | 514/616 |
| 5,756,548 | 5/1998 | Flitter et al. | 514/616 |

FOREIGN PATENT DOCUMENTS

| | | |
|---|---|---|
| 0 041 903 | 12/1990 | European Pat. Off. . |
| 7021320 | 2/1982 | Japan . |
| 58067657 | 4/1983 | Japan . |
| 1047028 | 11/1966 | United Kingdom . |
| 1 505 633 | 3/1978 | United Kingdom . |
| 1505633 | 3/1978 | United Kingdom . |
| 2244704 | 12/1991 | United Kingdom . |
| 2244704 | 8/1995 | United Kingdom . |
| WO 93/15047 | 8/1993 | WIPO . |
| WO 94/27584 | 12/1994 | WIPO . |
| 9528153 | 10/1995 | WIPO . |
| WO 95/28153 | 10/1995 | WIPO . |

OTHER PUBLICATIONS

R.W. Hartman et al., *Eur. J. Med. Chem.* (1994) 29, 807–817.

L.A. Errede, et al., *J. Org. Chem* (1977) 42(4) 656–658.

EPO Patent Abstracts of Japan, vol. 7, No. 155, and Derwent Abstract No. 83–52581K (Abstracts of Japanese Publication No. JP 58067657, published Apr. 22, 1983).

EPO Patent Abstracts of Japan, vol. 6, No. 90, and Derwent Abstract No. 82–20427E (Abstracts of Japanese Publication No. JP 57021320, published Feb. 4, 1982).

Chemical Abstract No. 61:13221d (1964) (Abstract 15 of M. Melandri, et al., *Bull. Chim. Farm.* 103, 475–489).

Chemical Abstract No. 58:4541a (1963) (Abstract of M. Itaya, et al., Yakugaku Zasshi (1962) 82, 634–639).

Patent Abstracts of Japan, vol. 006, No. 090 (C–104), May 27, 1982 & JP,A,57 021320 (Chugai Pharmaceut Co Ltd), Feb. 4, 1982, see abstract, see also Derwent abstract 82–20427E.

Patent Abstracts of Japan, vol. 007, No. 155 (C–175), Jul. 7, 1958 & JP,A,58 067657 (Chugai Seiyaku KK), Apr. 22, 1983, see abstract, see also Derwent abstract 83–52581K.

Banasik et al., "Specific inhibitors of poly(ADP–Ribose) synthetase and mono(ADP–ribosyl)transferase" *J. Biol. Chem.* (1992) 267:1569–1575.

Beal, M.F. in *Mitochondrial Dysfunction and Oxidative Damage in Neurogenerative Diseases*, R.G. Landes Publications Austin, TX, (1995) pp. 53–61 and 73–99.

Bishop et al., "Synthesis and in vitro evaluation of 2,3–dimethoxy–5–(fluoroalkyl)–substituted benzamides: high–affinity ligands for CNS dopamine $D_2$ receptors" *J. Med. Chem.* (1991) 34:1612–1624.

Burns, R.S. et al., "A Primate Model of Parkinsonism . . . " *Proc. Natl. Acad. Sci. USA* (1983) 80:4546–4550.

Calne, D.B., "Treatment of Parkinson's Disease" *NEJM* (Sep. 30, 1993) 329:1021–1027.

El Tayar, et al., "Interaction of neuroleptic drugs with rat striatal D–1 and D–2 dopamine receptors: a quantative structure—affinity relationship study" *Eur. J. Med. Chem.* (1988) 23:173–182.

Gerlach, M. et al., "MPTP Mechanisms of Neurotoicxity and the Implications for Parkinson's Disease" *European Journal of Pharmacology* (1991) 208:273–286.

Heikkila, R.E. et al., "Dopaminergic Neurotoxicity of 1–Methyl–4–Phenyl–1,2,5,6–Tetrahydropyridine in Mice" *Science* (June 29, 1984) 224:1451–1453.

Högberg et al., "Potential antipsychotic agents. 9. Synthesis and steroselective dopamine D–2 receptor blockade of a potent class of substituted (R)–N–[benzyl–2–pyrrolidinyl0methyl]benzamides. Relations to other side chain congeners" *J. Med. Chem* (1991) 34:948–955.

Kato, T., "Reaction of Triethyloxonium Fluoroborate with Acid Amide.III$^{1)}$ Formation of Quinazoline and 4H–3, 1–Benzoxazin–4–one Derivatives" *Chem. Pharm. Bull.* (1976) 24,3:431–436.

Katopodis et al., "Novel substrates and inhibitors of peptidylglycineα–amidating monooxygenase" *Biochemistry* (1990) 29:4541–4548.

(List continued on next page.)

Primary Examiner—Shailendra Kumar
Attorney, Agent, or Firm—Burns, Doane, Swecker & Mathis

[57] ABSTRACT

A group of benzamide compounds are disclosed. These materials are formed into pharmaceutical compositions for oral or intravenous administration to patients suffering from conditions such as Parkinson's disease which can exhibit themselves as progressive loss of central nervous system function. The pharmaceutical compositions can arrest or slow the progressive loss of function.

24 Claims, No Drawings

OTHER PUBLICATIONS

Langston, J.W., et al., "Chronic Parkinsonism in Humans Due to a Product of Meperidine–Analog Synthesis" *Science* (Feb. 25, 1983) 219,979–980.

Marsden, C.D., in "Review Article—Parkinson's Disease" *Lancet* (Apr. 21, 1990) 948–952.

Mizuno, Y., Mori, H., Kondo, T. "Potential of Neuroprotective Therapy in Parkinson's Disease" *CNS Drugs* (1994) 1:45–46.

Monković et al., "Potential non–dopaminergic gastronintestinal prokinetic agents in the series of substituted benzamides" *Eur. J. Med. Chem.* (1989) 24:233–240.

Rainnie et al., "Adenosine inhibition of mesopontine cholinergic neurons: implications for EEG arousal" *Science* (1994) 263:689–690.

Singer, T.P., et al., "Biochemical Events in the Development of Parkinsonism . . . " *J. Neurochem.* (1987) 1–8.

5,955,506

BENZAMIDES FOR NEURODEGENERATIVE DISORDER TREATMENT

This application is a 371 of PCT/US96/04538, filed Apr. 3, 1996.

FIELD OF THE INVENTION

This invention concerns benzamide compounds, pharmaceutical compositions containing these compounds, and their preparation and use to treat or protect against neurodegenerative conditions.

BACKGROUND INFORMATION

Neurodegenerative disease encompasses a range of seriously debilitating conditions including Parkinson's disease, amyotrophic lateral sclerosis (ALS, "Lou Gehrig's disease"), multiple sclerosis, Huntington's disease, Alzheimer's disease, diabetic retinopathy, multi-infarct dementia, macular degeneration and the like. These conditions are characterized by a gradual but relentless worsening of the patient's condition over time. The mechanisms and causes of these diseases are becoming better understood and a variety of treatments have been suggested. One of these neurodegenerative conditions, Parkinson's disease, is associated with abnormal dopamine depletion in selected regions of the brain.

Recent summaries of the state of understanding of Parkinson's disease are provided by Marsden. C. D., in "Review Article—Parkinson's Disease" *Lancet* (Apr. 21, 1990) 948–952 and Calne, D. B., in "Treatment of Parkinson's Disease" *NEJM* (Sep. 30, 1993) 329:1021–1027. As these reviews point out, dopamine deficiency was identified as a key characteristic of Parkinson's disease, and the destruction of the dopaminergic nigrostriatal pathway paralleled dopamine depletion in Parkinson's patients.

Rapid development of Parkinson's-like symptoms in a small population of illicit drug users in the San Jose, Calif. area was linked to trace amounts of a toxic impurity in the home-synthesized drugs. Subsequent studies in animal models, including monkeys, demonstrated that 1-methyl-4-phenyl-1,2,5,6-tetrahydropyridine (MPTP) was the cause of the Parkinson's-like symptoms which developed in the illicit drug users, as reported by J. W. Langston et al., in "Chronic Parkinsonism in Humans Due to a Product of Meperidine-Analog Synthesis" *Science* (Feb. 25, 1983) 219, 979–980. These early findings and the many studies that they stimulated led to the development of reliable models for Parkinson's disease, as reported by Heikkila, R. E., et al., in "Dopaminergic Neurotoxicity of 1-Methyl-4-Phenyl-1,2,5, 6-Tetrahydropyridine in Mice" *Science* (Jun. 29, 1984) 224:1451–1453; Burns, R. S., et al., in "A Primate Model of Parkinsonism . . . " *Proc. Natl. Acad. Sci USA* (1983) 80:4546–4550; Singer, T. P., et al., "Biochemical Events in the Development of Parkinsonism . . . " *J. Neurochem.* (1987) 1–8; and Gerlach, M. et al., "MPTP Mechanisms of Neurotoxicity and the Implications for Parkinson's Disease" *European Journal of Pharmacology* (1991) 208:273–286. These references and others describe studies to help explain the mechanism of how the administration of MPTP to animals gives rise to motor defects characteristic of Parkinson's disease. They clearly indicate that MPTP was the cause of the Parkinson's-like symptoms that developed in the humans who had used the tainted illicit drugs and that similar motor deficits were found in other primates and other test animals which had been dosed directly with MPTP. They further point out that the administration of MPTP induces a marked reduction in the concentration of dopamine in the test subjects.

These findings have led to the development of an assay for agents effective in treating dopamine-associated neurodegenerative disorders, such as Parkinson's disease. In this assay, test animals are given an amount of MPTP adequate to severely depress their dopamine levels. Test compounds are administered to determine if they are capable of preventing the loss of dopamine in the test animals. To the extent that dopamine levels are retained, a compound can be considered to be an effective agent for slowing or delaying the course of neurodegenerative disease, e.g., Parkinson's disease.

Another assay for agents effective in treating dopamine-associated neurodegenerative disorders has been developed. In this assay, the striatum of test animals is injected with the neurotoxicant, 6-hydroxydopamine. 6-Hydroxydopamine has a dopamine-depleting action and is widely accepted as a model for these conditions. Test compounds are administered to determine if they are capable of preventing or reducing the loss of dopamine in the test animals. Again, to the extent that dopamine levels are retained, a compound can be considered an effective agent.

Mitochondrial function is associated with many neurodegenerative diseases such as ALS, Huntington's disease, Alzheimer's disease, cerebellar degeneration, and aging itself (Beal, M. F. in *Mitochondrial Dysfunction and Oxidative Damage in Neurodegenerative Diseases,* R. G. Landes Publications Austin, Tex., 1995 at, for example, pages 53–61 and 73–99). Mitochondrial damage is the mechanism by which MPTP depletes dopamine concentrations in the striatum (Mizuno, Y., Mori, H., Kondo, T. in "Potential of Neuroprotective Therapy in Parkinson's Disease" *CNS Drugs* (1994) 1:45–46). Thus, an agent which protects from mitochondrial dysfunction caused by MPTP could be useful in treating diseases of the central nervous system in which the underlying cause is mitochondrial dysfunction.

Models are also available for determining the efficacy of materials in the treatment of other neurodegenerative conditions. For example, the efficacy of compounds against Alzheimer's disease can be determined in cell culture tests. In two such tests, compounds are evaluated for their ability to protect against the amyloid $\beta(25\text{-}35)$ or glutamate-induced neuronal cell loss in rat embryonic hippocampal neuronal/astrocytes cultures. In another test, compounds are evaluated for their ability to intervene in amyloid $\beta(1\text{-}40)$ beta pleated sheet formation. Compounds which have this effect can be considered candidates for treating Alzheimer's disease.

While other benzamide compounds are known, their utility heretofore has generally been as intermediates in chemical syntheses or in fields unrelated to the present invention. Slight structural changes yielded large differences in efficacy and toxicity. The vast majority of benzamide compounds have little or no activity in our screens. However, there are reports of biological activity for other, structurally different benzamides. These reports include:

El Tayar et al., "Interaction of neuroleptic drugs with rat striatal D-1 and D-2 dopamine receptors: a quantitative structure—affinity relationship study" *Eur. J. Med. Chem.* (1988) 23:173–182;

Monković et al., "Potential non-dopaminergic gastrointestinal prokinetic agents in the series of substituted benzamides" *Eur. J. Med. Chem.* (1989) 24:233–240;

Banasik et al., "Specific inhibitors of poly(ADP-Ribose) synthetase and mono(ADP-ribosyl)transferase" *J. Biol. Chem.* (1992) 267:1569–1575;

Bishop et al., "Synthesis and in vitro evaluation of 2,3-dimethoxy-5-(fluoroalkyl)-substituted benzamides: high-affinity ligands for CNS dopamine $D_2$ receptors" *J. Med. Chem.* (1991) 34:1612–1624;

Högberg et al., "Potential antipsychotic agents. 9. Synthesis and stereoselective dopamine D-2 receptor blockade of a potent class of substituted (R)-N-[benzyl-2-pyrrolidinyl)methyl]benzamides. Relations to other side chain congeners" *J. Med. Chem.* (1991) 34:948–955;

Katopodis et al., "Novel substrates and inhibitors of peptidylglycine α-amidating monooxygenase" *Biochemistry* (1990) 29:4541–4548; and Rainnie et al., "Adenosine inhibition of mesopontine cholinergic neurons: implications for EEG arousal" *Science* (1994) 263:689–690.

Other benzamide-containing pharmaceutical compositions and their use to treat or protect against neurodegenerative conditions were disclosed in commonly owned U.S. Pat. No. 5,472,983.

Statement of the Invention

Benzamide-based pharmaceutical compositions having activity against neurodegenerative diseases have now been discovered. These compositions include one or more of the acetamidobenzamide, aminobenzamide or nitrobenzamide compounds of Formula I as active agent in a pharmaceutically acceptable carrier.

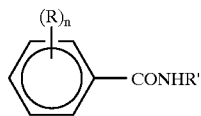

I

In Formula I R' is a saturated alkyl of from 3 to 5 carbon atoms, each R is independently —NH—CO—CH$_3$, —NO$_2$ or —NH$_2$, and n is 1 or 2, with the following provisos: 1) when n is 1 and R is —NO$_2$ at the 4 position of the ring, R' is not tert-butyl, iso-butyl, or propyl; 2) when n is 1 and R is —NO$_2$ at the 2 position of the ring, R' is not iso-butyl or propyl; and 3) when n is 2 and R' is tert-butyl and both Rs are —NO$_2$, the R groups are not at the 3 and 5 positions of the ring. The carrier is preferably an oral carrier but can be an injectable carrier as well. These pharmaceutical compositions can be in bulk form but more typically are presented in unit dosage form.

In a preferred embodiment the pharmaceutical compositions include one or more acetamidobenzamide compounds of Formula II as active agent. These compositions exhibit activity against Parkinson's disease as measured by their ability to prevent MPTP-induced and 6-hydroxydopamine-induced reduction of dopamine levels.

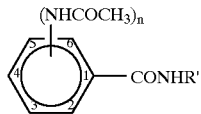

II

In Formula II, R' is a straight, branched or cyclic saturated alkyl of from 3 to 5 carbon atoms and n is 1 or 2.

Some of the benzamide compounds employed in these compositions are known compounds while others are novel. These novel compounds as well as some additional novel nitrobenzamides and aminobenzamides which are useful as chemical intermediates in the preparation of the active materials constitute additional aspects of this invention.

Those acetamidobenzamides of Formula II wherein R' is a straight, branched or cyclic saturated alkyl of from 3 to 5 carbon atoms and n is 1 or 2 but subject to the proviso that, when n is 1 and R' is either n-butyl or n-propyl, the acetamido group is not at the 2 position of the ring, when n is 1 the acetamido group is not at the 3 position of the ring and, when n is 2, the acetamido groups are not at the 3 and 5 positions of the ring, as compounds, constitute an aspect of the invention.

The following nitro- and aminobenzamides, as compounds, are another aspect of this invention: N-tert-amyl-4-nitrobenzamide (CPI1033), N-1,2-dimethylpropyl-4-nitrobenzamide (CPI1085), N-n-butyl-3-nitrobenzamide (CPI1135), N-n-pentyl-4-nitrobenzamide (CPI1140), N-2-methylbutyl4-nitrobenzamide (CPI1146), N-n-butyl-3,5-dinitrobenzamide (CPI1147), N-methylcyclopropyl-4-nitrobenzamide (CPI1164), N-n-butyl-2-nitrobenzamide (CPI1173), N-n-pentyl-2-nitrobenzamide (CPI1174), and N-methylcyclopropyl-4-aminobenzamide (CPI1240). (The "CPI . . . " numbers following each of these compound names and used throughout this specification are internal identification numbers. They are employed herein to simplify data presentation in the examples.)

In another aspect this invention provides a method for treating a patient suffering from a neurodegenerative condition and particularly a dopamine-associated neurodegenerative condition. This method involves administering to the patient an effective neurodegenerative condition-treating amount of one or more of the pharmaceutical compositions just described.

In another aspect this invention provides a method for treating a patient suffering from a condition characterized by progressive loss of central nervous system function. This method involves administering to the patient with loss of central nervous system function an effective amount of one or more of the pharmaceutical compositions just described.

In a most important aspect this invention provides a method for treating a patient suffering from a progressive loss of central nervous system function associated with Parkinson's disease. This method involves administering (preferably orally) to the patient with progressive loss of central nervous system function an effective amount of one or more of the pharmaceutical compositions just described.

In another aspect this invention provides a method for treating a patient suffering from a condition characterized by progressive loss of nervous system function due to mitochondrial dysfunction. This method involves administering to the patient with loss of central nervous system function an effective amount of one or more of the pharmaceutical compositions just described.

In a further aspect, this invention provides methods for preparing the compounds of Formulae I and II. These methods generally involve condensing an alkyl amine of from 3 to 5 carbon atoms with a mono or dinitro benzoyl halide having the nitro configuration corresponding to the nitro, amine or acetamide substitution desired in the final compound, optionally, reducing the nitro groups, and, optionally, converting the amino benzamides to acetamidobenzamides by reaction with an acetyl halide.

DETAILED DESCRIPTION OF THE INVENTION

The Benzamides

This invention employs certain acetamidobenzamides, aminobenzamides and nitrobenzamides as active pharmaceutical agents. The acetamidobenzamides are described by Formula I when R is an acetamido group and by Formula II. In these formulae, R' is a saturated alkyl of from 3 to 5 carbon atoms and n is 1 or 2.

The acetamido group (or groups) may be found anywhere on the ring. Preferred embodiments include when n is 1 and the acetamido group is at the 2, 3 or 4 position of the ring and when n is 2 and the acetamido groups are at the 2 and 3, 2 and 4, 2 and 5, 2 and 6, 3 and 4, or 3 and 5 positions of the ring.

With respect to the alkyl substituents, R', compounds wherein R' is an alkyl which does not have a hydrogen on the alpha carbon, that is, the carbon which bonds to the nitrogen of the ring, are preferred. Examples of these preferred R' groups are tert-butyl and tert-amyl.

Acetamidobenzamides of Formula I of particular interest are:
N-tert-butyl-4-acetamidobenzamide (CPI1189),
N-iso-propyl-4-acetamidobenzamide (CPI1232),
N-tert-amyl-4-acetamidobenzamide (CPI1233),
N-tert-butyl-3-acetamidobenzamide (CPI1234), and
N-methylcyclopropyl-4-acetamidobenzamide (CPI1241).

N-tert-butyl-4-acetamidobenzamide (CPI1189) is the most preferred acetamidobenzamide.

There are numerous novel compounds among this family of acetamidobenzamides. More particularly, these are the acetamidobenzamides of Formula I (when R is acetamido) and Formula II where n is 1 or 2 and R' is a saturated alkyl of from 3 to 5 carbon atoms subject to the proviso that, when n is 1 and R' is either n-butyl or n-propyl, the acetamido group is not at the 2 position of the ring, when n is 1 the acetamido group is not at the 3 position of the ring and, when n is 2, the acetamido groups are not at the 3 and 5 positions of the ring. Again, the five acetamidobenzamides specifically listed as preferred active agents are preferred novel compounds, with CPI1189 being the most preferred.

The aminobenzamides and nitrobenzamides employed as active agents are described by Formula I when R is an amino or nitro group. In these formulae, R' is a saturated alkyl of from 3 to 5 carbon atoms and n is 1 or 2 subject to the same preferences for substituents and their positions set forth with reference to the acetamidobenzamides and further subject to the provisos that 1) when n is 1 and R is —NO$_2$ at the 4 position of the ring, R' is not tert-butyl, iso-butyl, or propyl; 2) when n is 1 and R is —NO$_2$ at the 2 position of the ring, R' is not iso-butyl or propyl; and 3) when n is 2 and R' is tert-butyl and both Rs are 13 NO$_2$, the R groups are not at the 3 and 5 positions of the ring. Aminobenzamides and nitrobenzamides of Formula I of particular interest as active agents are:
N-iso-propyl4-nitrobenzamide (CPI1026),
N-ten-butyl-3-nitrobenzamide (CPI1034),
N-tert-butyl-2-nitrobenzamide (CPI1035),
N-n-butyl-4-nitrobenzamide (CPI1045),
N-n-propyl-4-nitrobenzamide (CPI1047),
N-tert-butyl-3,5-dinitrobenzamide (CPI1049),
N-1-methylpropyl-4-nitrobenzamide (CPI1084),
N-tert-butyl4-aminobenzamide (CPI1160) and
N-tert-butyl-3-aminobenzamide (CPI1248).

There are novel compounds among this family of aminobenzamides and nitrobenzamides and there are additional novel compounds which serve as intermediates to these materials and the above-described acetamidobenzamides. More particularly, these novel aminobenzamides and nitrobenzamides are:
N-tert-amyl-4-nitrobenzamide (CPI1033),
N- 1,2-dimethylpropyl-4-nitrobenzamide (CPI1085),
N-n-butyl-3-nitrobenzamide (CPI135),
N-n-pentyl4-nitrobenzamide (CPI1140),
N-2-methylbutyl-4-nitrobenzamide (CPI1146),
N-n-butyl-3,5-dinitrobenzamide (CPI1147),
N-methylcyclopropyl-4-nitrobenzamide (CPI1164),
N-n-butyl-2-nitrobenzamide (CPI1173),
N-n-pentyl-2-nitrobenzamide (CPI1174), and
N-methylcyclopropyl-4-aminobenzamide (CPI1240).

When the benzamide compound contains an amino group, such as is the Vase with CPI 1240, the amine functionality can be present as such or as a salt. In the salt form the amino is protonated to the cation form in combination with a pharmaceutically acceptable anion, such as chloride, bromide, iodide, hydroxyl, nitrate, sulfonate, methane sulfonate, acetate, tartrate, oxalate, succinate, or palmoate. When these aminobenzamides are referred to it is to be understood that these salts are included as well.

Commonly owned U.S. Pat. No. 5,472,983, referred to above, discloses several benzamides useful in treating neurodegenerative diseases based on their protective action in the MPTP mouse model of Parkinson's disease. The compound N-tert-butyl 4-acetamidobenzamide (CPI1189) of the present invention is an in vivo biotransformation product of one of these benzamides (N-tert-butyl 4-nitrobenzamide (CPI1020)) which has been found in the blood of rats and mice to which CPI1020 has been administered orally. This compound is likely formed in the body by reduction of the ring nitro of CPI1020 to an amino moiety (CPI1160) followed by acetylation of the amino function.

The compounds of the present invention, as exemplified by CPI1189, are much more potent than CPI1020 (approximately 10 times as potent) in protecting mice from dopamine reduction in the striatum induced by s.c. treatment with MPTP. Based on structurally similar molecules such as acetaminophen which contain an acetamido functionality, they should also be safer than CPI1020 because they would not be metabolized in the body to result in metabolites containing hydroxylamines (likely to be Ames positive) nor would they be likely to result in amino metabolites which may have cardiovascular and/or anorexic effects.

Pharmaceutical Compositions

The benzamide compounds of Formulae I and II noted above are formulated into pharmaceutical compositions suitable for oral or other appropriate routes of administration such as parenteral adminstration by injection or intraveneous delivery.

Pharmaceutical compositions using the compounds N-tert-butyl 4-acetamidobenzamide (CPI1189), N-tert-butyl-3-acetamidobenzamide (CPI1234), N-tert-amyl-4-acetamidobenzamide (CPI1233), N-tert-butyl4-aminobenzamide (CPI1160), N-tert-butyl-3-nitrobenzamide (CPI1034), and N-tert-butyl-3-aminobenzamide (CPI1248) are preferred with compositions based on CPI1189 being most preferred at this time.

The compositions for oral administration can take the form of bulk liquid solutions or suspensions, or bulk powders. More commonly, however, the compositions are presented in a unit dosage form to facilitate accurate dosing. Typical unit dosage forms include prefilled, premeasured ampules or syringes of the liquid compositions or pills, tablets, capsules or the like in the case of solid compositions. In such compositions, the benzamide compound is usually a minor component (0.1 to say 50% by weight or preferably from about 1 to about 40% by weight) with the remainder being various vehicles or carriers and processing aids helpful for forming the desired dosing form. A liquid form may include a suitable aqueous or nonaqueous vehicle with buffers, suspending and dispensing agents, colorants, flavors and the like.

A solid form may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

In the case of injectable compositions, they are commonly based upon injectable sterile saline or phosphate-buffered saline or other injectable carriers known in the art. Again the active benzamide is typically a minor component, often being from about 0.05 to 10% by weight with the remainder being the injectable carrier and the like. The liquid materials can be solutions or suspensions.

These components for orally administrable or injectable compositions are merely representative. Other materials as well as processing techniques and the like are set forth in Part 8 of *Remington's Pharmaceutical Sciences,* 17th edition, 1985, Mack Publishing Company, Easton, Pa., which is incorporated by reference.

One can also administer the compounds of the invention in sustained release forms or from sustained release drug delivery systems. A description of representative sustained release materials can be found in the incorporated materials in *Remington's Pharmaceutical Sciences.*

Conditions Treated and Treatment Regimens

The conditions treated with the benzamide-containing pharmaceutical compositions may be classed generally as neurodegenerative conditions. These include conditions characterized by protracted low grade stress upon the central nervous system and gradual progressive loss of central nervous system function. These conditions include Parkinson's disease, amyotrophic lateral sclerosis (ALS, "Lou Gehrig's disease"), multiple sclerosis, Huntington's disease, Alzheimer's disease, diabetic retinopathy, multi-infarct dementia, macular degeneration and the like. Each of these conditions is characterized by a progressive loss of function. The benzamide compound-containing pharmaceutical compositions of this invention, when administered orally or by injection such as intravenously, can slow and delay and possibly even to some extent reverse the loss of function.

Injection dose levels for treating these conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

With these neurodegenerative conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 1 to about 20 mg/kg of benzamide, with preferred doses each providing from about 1 to about 10 mg/kg and especially about 1 to about 5 mg/kg.

Of course, one can administer the benzamide compound as the sole active agent or one can administer it in combination with other agents, including other active benzamide compounds.

Methods of Preparation of Compounds

The benzamide compounds of this invention can be prepared using commonly available starting materials and readily achievable reactions.

One representative preparation route, which is illustrated with tert-butyl amine, but which may be used with any alkyl amine, involves the following reactions:

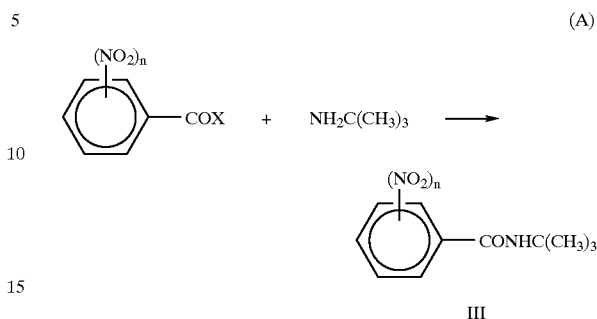

where X is halo such as I, Br, F or Cl.

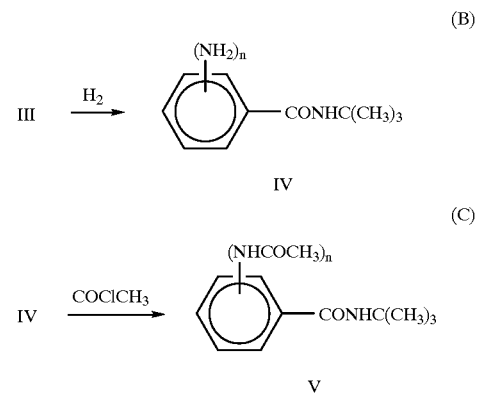

In step (A) the N-tert-butyl nitrobenzamides (III) are formed. This reaction should be carried out at temperatures below 10° C.

This step (A) yields as benzamides III, the compounds of the invention where R is —NO$_2$.

In step (B) the nitro groups in the mono- or di-nitro benzamide III are subjected to reduction. This is commonly carried out with a reducing agent such as hydrazine and an appropriate catalyst such as a heterogeneous platinum, iron oxide hydroxide, palladium or nickel catalyst, typically on a support, or with hydrogen gas and a catalyst.

This step (B) yields as benzamides IV, the compounds of the invention where R is NH$_2$.

In step (C) the amino-benzamides IV are converted to acetamidobenzamides V by reaction with an acetyl halide such as acetylchloride. This reaction is carried out in the presence of a mild base and at low to ambient temperatures such as −20° C. to +20° C. This yields the compounds of the invention where R is acetamido.

Alternate synthetic schemes may also be used to prepare the compounds of the present invention. Examples of these alternate routes are set forth below using CPI1189 as the representative compound. Other compounds may be prepared using these alternate methods by starting with appropriate starting materials, such as 2- or 3-amino- or nitro-benzonitrile or 2,3-, 2,4-, 2,5-, 2,6-, 3,4- or 3,5-diamino- or dinitro-benzonitrile and the appropriate alcohol (Alternate Route 1) or similarly substituted toluene compounds and the appropriate alkyl amine (Alternate Route 3).

Alternate Route 1

This route begins with acetylation of, for example, 4-aminobenzonitrile (A) to compound (B) using standard methods. Acid hydrolysis of tert-butanol in the presence of 4-acetamidobenzonitrile (B), provides a feasible synthetic pathway to CPI1189.

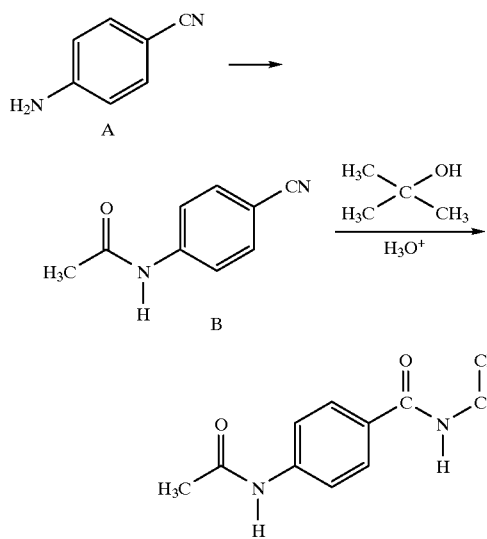

Alternate Route 2

Acetylation, using standard methods, of the inexpensive starting material PABA (C) affords a cheap method to produce 4-acetamidobenzoic acid (D). Conversion of (D) to the acid chloride (E) using standard methods (e.g., SOCl$_2$) and subsequent amidation using standard methods, such as those described previously, produces CPI1189 from inexpensive raw materials.

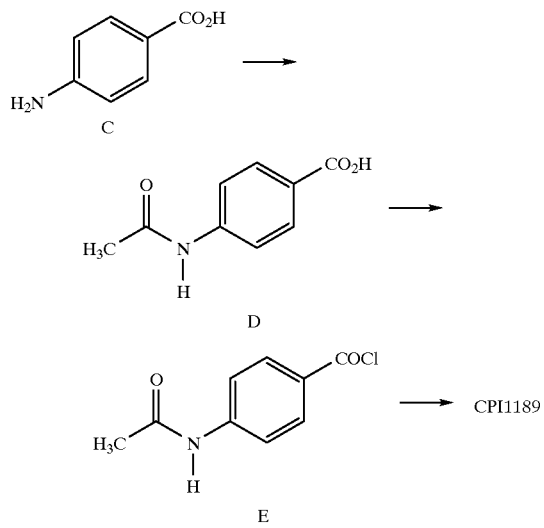

Alternate Route 3

Another method for the preparation of the compounds of the present invention begins with acetylation, using standard methods, of, for example, paratoluidine (F) to 4-acetamidotoluene (G). The synthetic intermediate (G) may be converted to 4-acetamidobenzoic acid (D) with common oxidizing agents (e.g., KMnO$_4$) and subsequently transformed to CPI1189 as outlined in Alternate Route 2.

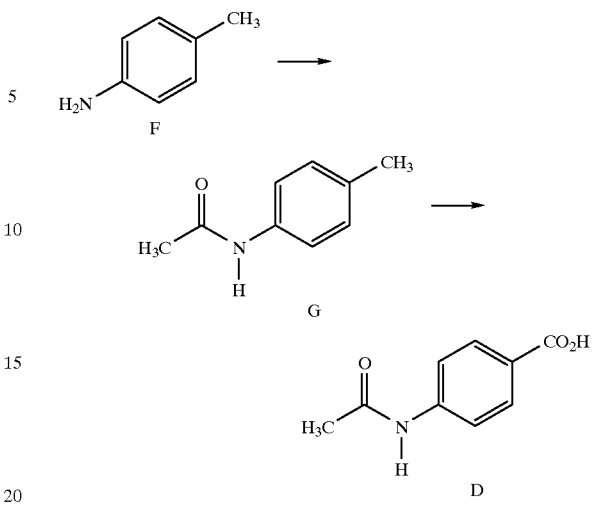

Examples

The invention will be further described by the following Examples. These are provided to illustrate several preferred embodiments of the invention but are not to be construed as limiting its scope which is, instead, defined by the appended claims. Examples 1 to 19 demonstrate the preparation of acetamidobenzamides, as well as nitro- and aminobenzamides, which are representative of the benzamide compounds employed in the compositions and methods of this invention. Examples 20 to 24 demonstrate the preparation of pharmaceutical compositions based on the compounds. Thereafter biological test results illustrating the activity of the compositions of the invention are provided.

Example 1

Preparation of N-tert-butyl4-aminobenzamide (CPI1160)

tert-Butyl amine (14.6 g, 0.200 mole) was stirred in ethyl acetate (150 mL, purified by washing with 5% sodium carbonate solution, saturated sodium chloride solution, drying over anhydrous magnesium sulfate, and filtering through fluted filter paper) and cooled to 5° C. with an ice bath. 4-nitrobenzoyl chloride (18.6 g, 0.100 mole) in purified ethyl acetate (75 mL) was added dropwise at such a rate to maintain the temperature below 10° C. The ice bath was removed upon complete addition of benzoyl chloride solution and the reaction stirred for 4 hours. The reaction mixture was then filtered on a Büchner funnel, the filtrate washed three times with 5 % HCl, once with saturated sodium chloride, dried over anhydrous magnesium sulfate, filtered through fluted filter paper, and the solvent stripped off leaving white crystalline product. The product was dried in a vacuum oven at 24 mm and 45° C. for 14 hours. This procedure produced 17.13 g of crystals of N-tert-butyl-4-nitrobenzamide (CPI1020) (77% yield), mp 162–163° C. Proton nuclear magnetic resonance (89.55 MHz in CDCl$_3$) showed absorptions at 8.257 ppm (d, 8.8 Hz, 2H; 3,5-aryl H); 7.878 ppm (d, 8.8 Hz, 2H; 2,6-aryl H); 6.097 ppm (bs, 1H; N—H); 1.500 ppm (s, 9H; tert-butyl H).

Palladium on carbon (5%, 75 mg) was added to CPI-1020 (5 g, 22.5 mmole) in 95% ethanol at 55° C. A solution of hydrazine (1.2 mL) in 95% ethanol (10 mL) was added dropwise over 30 min. and more Pd/C added (75 mg). The reaction was refluxed 3 hours, hydrazine (0.5 g) in 95% ethanol (5 mL) was added and the reaction was refluxed for another hour. The reaction was filtered on a buchner funnel, the volume of solvent reduced under vacuum, and extracted with dichloromethane. The combined extracts were dried over magnesium sulfate and solvent stripped, leaving 3.90 g of N-tert-butyl4-aminobenzamide (CPI1160) (90% yield), melting point 125–127° C. 90 MHz proton NMR (in $CDCl_3$) showed absorbances at 7.290 ppm (2H, d, 8.8 Hz; 2,6 aryl H); 6.368 ppm (2H, d, 8.8 Hz; 3,5 aryl H); 5.45 ppm (1 H, bs; NHC=O); 3.727 ppm (2H, bs; aryl-$NH_2$); 1.186 ppm (9 H, s; t-butyl H).

Example 2

Preparation of N-tert-butyl4-acetamidobenzamide (CPI1189)

Acetyl chloride (0.45 g, 5.7 mmole) in ethyl acetate (25 mL) was added dropwise to CPI-1160 (1.0 g, 5.2 mmole) and triethyl amine (0.58 g, 5.7 mmole) in ethyl acetate at 3° C. at such a rate to maintain the temperature below 10° C. The reaction was allowed to warm to room temperature, stirred 1 hour, and washed with 5% HCl. Recrystallization from acetone gave 1.08 g N-tert-butyl-4-acetamidobenzamide (CPI1189)(89% yield), melting point 119–121° C. 90 MHz proton NMR (in DMSO-d6) showed absorbances at 9.726 ppm (1H, bs, N—H); 7.715 ppm (4H, dd, 4.4 Hz; aryl H); 7.295 ppm (1 H, bs; NH); 2.844 ppm (3H, s; $CH_3CO$); 1.448 ppm (9 H, s; t-butyl H).

Example 3

Preparation of N-tert-butyl-3-nitrobenzamide (CPI1034) N-tert-butyl-3-aminobenzamide (CPI1248) and N-tert-butyl-3-acetamidobenzamide (CPI1234)

The amidation procedures of Example 1 were followed using 3-nitrobenzoyl chloride instead of 4-nitrobenzoyl chloride. This gave N-tert-butyl-3-nitrobenzamide (CPI1034) in 92% yield, melting point 123–125° C. Proton NMR (in $CDCl_3$) showed absorptions at 8.517 ppm (2-aryl H, s, 1H); 8.337 ppm (4-aryl H, d, 8.8 Hz, 1H); 8.121 ppm (6-aryl H, d, 6.4 Hz, 1H); 7.618 ppm (5-aryl H, m, 1H); 6.032 ppm (N—H, bs, 1H); 1.484 ppm (t-butyl H, s, 9 H).

Iron (III) oxide hydroxide catalyzed hydrazine reduction produced N-tert-butyl-3-aminobenzamide (CPI1248) in 53% yield, melting point 118–120° C. Proton NMR (in $CDCl_3$) showed absorbances at 7.088 ppm (4–6-aryl H, m, 3 H); 6.794 ppm (2-aryl H, s, 1H); 5.902 ppm (N—H, bs, 1H); 3.145 ppm (aryl N—H, bs, 2H); 1.458 ppm (t-butyl H, s, 9 H).

Acetylation of CPI1248 as described in Example 2 gave N-tert-butyl-3-acetamidobenzamide (CPI1234) in 75% yield, melting point 194–195° C. Proton NMR (in $CDCl_3$) showed absorptions at 7.778 ppm (4–6-aryl H, m, 3 H); 7.392 ppm (2-aryl H, s, 1H); 6.08 ppm (N—H, bs, 1H); 2.174 ppm (acetyl $CH_3$, s, 9 H); 1.500 ppm (t-butyl H, s, 9 H).

Example 4

Preparation of N-tert-butyl-2-nitrobenzamide (CPI1035) and N-tert-butyl-2-acetamidobenzamide The method of Example 3 is repeated using 2-nitrobenzoyl chloride in the amidation step. This yields N-tert-butyl-2-nitrobenzamide (CPI1035).

Reduction of the nitrobenzamide with hydrazine yields N-tert-butyl-2-aminobenzamide.

Acetylation of the aminobenzamide yields N-tert-butyl-2-acetamidobenzamide.

Example 5

Preparation of N-iso-propyl-4-nitrobenzamide (CPI1026) and N-iso-propyl-4-acetamidobenzamide (CPI1232)

The method of Example 3 is repeated using 4-nitrobenzoyl chloride and iso-propyl amine in the amidation step. This yields N-iso-propyl-4-nitrobenzamide (CPI1026).

Reduction of the nitrobenzamide with hydrazine yields N-iso-propyl-4-aminobenzamide.

Acetylation of the aminobenzamide yields N-iso-propyl-4-acetamidobenzamide (CPI1232).

Example 6

Preparation of N-tert-amyl4-nitrobenzamide (CPI1033) and N-tert-amyl-4-acetamidobenzamide (CPI1233)

The method of Example 3 is repeated using 4-nitrobenzoyl chloride and tert-amyl amine in the amidation step. This yields N-tert-amyl-4-nitrobenzamide (CPI1033).

Reduction of the nitrobenzamide with hydrazine yields N-tert-amyl-4-aminobenzamide.

Acetylation of the aminobenzamide yields N-ten-amyl4-acetamidobenzamide (CPI1233).

Example 7

Preparation of N-iso-butyl-4-acetamidobenzamide

The method of Example 3 is repeated using 4-nitrobenzoyl chloride and iso-butyl amine in the amidation step. This yields N-iso-butyl-4-nitrobenzamide (CPI1044).

Reduction of the nitrobenzamide with hydrazine yields N-iso-butyl-4-aminobenzamide.

Acetylation of the aminobenzamide yields N-iso-butyl-4-acetamidobenzamide.

Example 8

Preparation of N-n-butyl-4-nitrobenzamide (CPI1045) and N-n-butyl-4-acetamidobenzamide The method of Example 3 is repeated using 4-nitrobenzoyl chloride and n-butyl amine in the amidation step. This yields N-n-butyl-4-nitrobenzamide (CPI1045).

Reduction of the nitrobenzamide with hydrazine yields N-n-butyl-4-aminobenzamide.

Acetylation of the aminobenzamide yields N-n-butyl-4-acetamidobenzamide.

Example 9

Preparation of N-n-propyl4-nitrobenzamide (CPI1047) and N-n-propyl-4-acetamidobenzamide The method of Example 3 is repeated using 4-nitrobenzoyl chloride and n-propyl amine in the amidation step. This yields N-n-propyl-4-nitrobenzamide (CPI1047).

Reduction of the nitrobenzamide with hydrazine yields N-n-propyl4-aminobenzamide.

Acetylation of the aminobenzamide yields N-n-propyl4-acetamidobenzamide.

Example 10

Preparation of N-1,2-dimethylpropyl-4-nitrobenzamide (CPI1085) and N-1,2-dimethylpropyl-4-acetamidobenzamide The method of Example 3 is repeated using 4-nitrobenzoyl chloride and 1,2-dimethylpropyl amine in the amidation step. This yields N-1,2-dimethylpropyl-4-nitrobenzamide (CPI1085).

Reduction of the nitrobenzamide with hydrazine yields N-1,2-dimethylpropyl-4-aminobenzamide.

Acetylation of the aminobenzamide yields N-1,2-dimethylpropyl4-acetamidobenzamide.

Example 11

Preparation of N-n-pentyl-4-nitrobenzamide (CPI1140) and N-n-pentyl-4-acetamidobenzamide The method of Example 3 is repeated using 4-nitrobenzoyl chloride and n-pentyl amine in the amidation step. This yields N-n-pentyl-4-nitrobenzamide (CPI1140).

Reduction of the nitrobenzamide with hydrazine yields N-n-pentyl4-aminobenzamide.

Acetylation of the aminobenzamide yields N-n-pentyl-4-acetamidobenzamide.

Example 12

Preparation of N-2-methylbutyl-4-nitrobenzamide (CPI1146) and N-2-methylbutyl-4-acetamidobenzamide The method of Example 3 is repeated using 4-nitrobenzoyl chloride and 2-methylbutyl amine in the amidation step. This yields N-2-methylbutyl-4-nitrobenzamide (CPI1146).

Reduction of the nitrobenzamide with hydrazine yields N-2-methylbutyl-4-aminobenzamide.

Acetylation of the aminobenzamide yields N-2-methylbutyl-4-acetamidobenzamide.

Example 13

Preparation of N-n-pentyl-2-nitrobenzamide (CPI1174) and N-n-pentyl-2-acetamidobenzamide The method of Example 3 is repeated using 2-nitrobenzoyl chloride and n-pentyl amine in the amidation step. This yields N-n-pentyl-2-nitrobenzamide (CPI1174).

Reduction of the nitrobenzamide with hydrazine yields N-n-pentyl-2-aminobenzamide.

Acetylation of the aminobenzamide yields N-n-pentyl-2-acetamidobenzamide.

Example 14

Preparation of N-tert-butyl-2,3-diacetamidobenzamide

The method of Example 3 is repeated using 2,3-dinitrobenzoyl chloride in the amidation step. This yields N-tert-butyl-2,3-dinitrobenzamide.

Reduction of the nitrobenzamide with hydrazine yields N-tert-butyl-2,3-diaminobenzamide.

Acetylation of the aminobenzamide yields N-tert-butyl-2,3-diacetamidobenzamide.

Example 15

Preparation of N-tert-amyl-2,4-diacetamidobenzamide

The method of Example 3 is repeated using 2,4-dinitrobenzoyl chloride and tert-amyl amine in the amidation step. This yields N-tert-amyl-2,4-dinitrobenzamide.

Reduction of the nitrobenzamide with hydrazine yields N-tert-amyl-2,4-diaminobenzamide.

Acetylation of the aminobenzamide yields N-tert-amyl-2,4-diacetamidobenzamide.

Example 16

Preparation of N-tert-butyl-2,5-diacetamidobenzamide

The method of Example 3 is repeated using 2,5-dinitrobenzoyl chloride in the amidation step. This yields N-tert-butyl-2,5-dinitrobenzamide.

Reduction of the nitrobenzamide with hydrazine yields N-tert-butyl-2,5-diaminobenzamide.

Acetylation of the aminobenzamide yields N-tert-butyl-2,5-diacetamidobenzamide.

Example 17

Preparation of N-tert-butyl-2.6-diacetamidobenzamide

The method of Example 3 is repeated using 2,6-dinitrobenzoyl chloride in the amidation step. This yields N-tert-butyl-2,6-dinitrobenzamide.

Reduction of the nitrobenzamide with hydrazine yields N-tert-butyl-2,6-diaminobenzamide.

Acetylation of the aminobenzamide yields N-tert-butyl-2,6-diacetamidobenzamide.

Example 18

Preparation of N-tert-butyl-3,4-diacetamidobenzamide

The method of Example 3 is repeated using 3,4-dinitrobenzoyl chloride in the amidation step. This yields N-tert-butyl-3,4-dinitrobenzamide.

Reduction of the nitrobenzamide with hydrazine yields N-tert-butyl-3,4-diaminobenzamide.

Acetylation of the aminobenzamide yields N-tert-butyl-3,4-diacetamidobenzamide.

Example 19

Preparation of N-tert-butyl-3,5-diacetamidobenzamide

The method of Example 3 is repeated using 3,5-dinitrobenzoyl chloride in the amidation step. This yields N-tert-butyl-3,5-dinitrobenzamide.

Reduction of the nitrobenzamide with hydrazine yields N-ten-butyl-3,5-diaminobenzamide.

Acetylation of the aminobenzamide yields N-tert-butyl-3,5-diacetamidobenzamide.

Preparation of Pharmaceutical Compositions

Example 20

The compound of Example 1 is admixed as a dry powder with a dry gelatin binder in an approximate 1:2 weight ratio.

A minor amount of magnesium stearate is added as a lubricant. The mixture is formed into 240–270 mg tablets (80–90 mg of active benzamide) in a tablet press. If these tablets were administered to a patient suffering from a dopamine-associated neurodegenerative condition on a daily, twice daily or thrice daily regimen they would slow the progress of the patient's disease.

Example 21

The compound of Example 2 is admixed as a dry powder with a starch diluent in an approximate 1:1 weight ratio. The mixture is filled into 250 mg capsules (125 mg of active benzamide). If these capsules were administered to a patient suffering from a dopamine-associated neurodegenerative condition on a daily, twice daily or thrice daily regimen they would slow the progress of the patient's disease.

Example 22

The compound of Example 3 is suspended in a sweetened flavored aqueous medium to a concentration of approximately 50 mg/ml. If 5 mls of this liquid material was administered to a patient suffering from a dopamine-associated neurodegenerative condition on a daily, twice daily or thrice daily regimen they would slow the progress of the patient's disease.

Example 23

The compound of Example 4 is admixed as a dry powder with a dry gelatin binder in an approximate 1:2 weight ratio. A minor amount of magnesium stearate is added as a lubricant. The mixture is formed into 450–900 mg tablets (150–300 mg of active benzamide) in a tablet press. If these tablets were administered to a patient suffering from a dopamine-associated neurodegenerative condition on a daily, twice daily or thrice daily regimen they would slow the progress of the patient's disease.

Example 24

The compound of Example 14 is dissolved in a buffered sterile saline injectable aqueous medium to a concentration of approximately 5 mg/ml. If 50 mls of this liquid material was administered to a patient suffering from a dopamine-associated neurodegenerative condition such as Parkinson's disease on a daily, twice daily or thrice daily regimen this dose would slow the progress of the patient's disease.

It will be appreciated that any of the compounds of Formula I could be employed in any of these representative formulations, and that any of these formulations could be administered in any of these manners so as to treat any of the neurodegenerative conditions described in this specification.

Parkinson's Disease Screening Methods

Dopamine Depletion Studies (MPTP Model)

C57BL/6J mice were pretreated with either vehicle (1% methyl cellulose) or a drug (p.o.) 30 min before MPTP. MPTP was dissolved in isotonic saline (0.9%) and given subcutaneously as a single dose of 15 mg free base/kg body weight to produce a reduction in striatal dopamine to about 0.5 nanomoles/mg protein. Groups of mice (n=8–10 per group) received either vehicle plus saline, vehicle plus MPTP, or drug plus MPTP. Seventy two hours after receiving MPTP, mice were sacrificed using cervical dislocation and the striata were excised. The tissue was homogenized in 0.4 N perchloric acid, centrifuged, and the supernatant analyzed by high performance liquid chromatography/electro-chemical detection (HPLC/ED) for dopamine levels. Supernatants were stored in a −90° C. freezer between the time of collection and analysis.

The drugs were combined with methyl cellulose and were homogenized in water for dosing. The dosage amount ranged from 10 to 50 mg/kg for CPI1160, CPI1189 and CPI1234, and from 50 to 100 mg/kg for CPI1020.

The results of representative experiments are provided in Tables 1 and 2. The results in Table 1 demonstrate that the compositions of this invention, as exemplified by CPI1160, CPI1189, and CPI1234 were effective in preventing dopamine depletion following MPTP challenge.

TABLE 1

Efficacy of CPI 1189, 1160, and 1234 at 30 mg/kg in the 15 mg/kg MPTP Model.

| COMPOUND | DOPAMINE/MG PROTEIN ± S.E.M. | % NON-MPTP CONTROL |
|---|---|---|
| methyl cellulose | 0.72 ± .05 | 54.1 |
| CPI1160 | 1.25 ± .05 | 93.9 |
| CPI1234 | 1.02 ± .05 | 76.7 |
| methyl cellulose | 0.56 ± .07 | 36.4 |
| CPI1189 | 1.37 ± .14 | 89.7 |

For comparison purposes the same tests were run on compositions based on CPI1020, a closely related benzamide compound. Results are shown in Table 2. At 50 mg/kg, CPI1189 offered complete protection from the neurotoxic action of MPTP (105% of control) while CPI1020 was not as effective (56% of control).

TABLE 2

Comparison of the Efficacies of CPI1189 and CPI1020 at 50 mg/kg in the 15 mg/kg MPTP Model.

| | DOPAMINE, nM/MG ± S.E.M. | | |
|---|---|---|---|
| COMPOUND | Test Compound | Standard* | Protection, % |
| CPI1020 | 0.58 ± .14 | 1.035 ± .099 | 56 |
| CPI1189 | 1.57 ± .11 | 1.536 ± .178 | 105 |

*methyl cellulose control

This test procedure was repeated on a number of other materials of this invention. The results are provided in Table 3 and show that other benzamides of the invention exhibit protective properties:

TABLE 3

Protective Effects of Benzamides in MPTP Dopamine Depletion Test

| Test Compound | Degree of Protection, % |
|---|---|
| 1160 | 94 |
| 1232 | 70 |
| 1233 | 40 |
| 1234 | 77 |
| 1241 | 40 |

Long Term Protective Effect Test

Additional studies were carried out to determine the long-term effect on dopamine depletion of the compounds of the invention. Using the general test method described above, C57BL/6J mice were pretreated with either vehicle or test compound and MPTP and then sacrificed either 3 or 14 days after dosing. The results are given in Table 4.

TABLE 4

CPI-1189 Efficacy in the MPTP Model
Effect of Post Dose Sac Time on Striatal Dopamine Concentrations.

| Treatment | Percent of Methyl Cellulose/Saline Control |
|---|---|
| Methyl Cellulose/MPTP (3 Day Sac) | 67.5 |
| CPI-1189/MPTP (3 Day Sac) | 100 |
| Methyl Cellulose/MPTP (14 Day Sac) | 75.8 |
| CPI-1189/MPTP (14 Day Sac) | 96.7 |

The results from this experiment show that CPI-1189 is able to protect against MPTP induced dopamine depletion in animals sacrificed at both three days post MPTP and fourteen days post MPTP. This suggests that CPI-1189's protective effect is due to neuroprotection rather than to a transient effect on dopamine metabolism.

Dopamine Depletion Studies (6-Hydroxydoamine Model)

Tests were conducted to assess the ability of CPI-1189 to protect against 6-hydroxydopamine-induced damage. This is a widely accepted model for Parkinson's disease in which 6-hydroxydopamine is believed to produce its toxic effects by inducing oxidative stress. 6-hydroxydopamine has been used extensively since the 1960's as a neurotoxicant. Because 6-hydroxydopamine primarily affects catecholaminergic neurons, it has been mainly used for the experimental study of Parkinson's disease. The compound has had widespread use as a means of administering unilateral lesions in the nigrastriatal system. Animals treated with this toxin show biochemical and behavioral alterations that can be measured and probed pharmacologically to assess both the severity of the lesion and to determine the effect of potential therapeutic interventions.

The protective dose response of CPI-1189 to 6-hydroxydopamine-induced damage to the nigrastriatal system was determined. Damage to the nigrastriatal system was measured in terms of striatal dopamine levels.

Acclimated male Sprague Dawley rats, 55 to 120 days of age were used.

6-hydroxy-dopamine (Research Biochemicals Incorporated) was prepared in a 0.9% NaCl solution containing 0.1 mg/ml ascorbic acid on the morning of the experiment.

Milled CPI-1189 (particle size ≦106μ) was formulated in a 1% methyl cellulose suspension on the morning of the treatment. CPI-1189 was administered orally at a dosing volume of 0.0005 ml/g using a 3.0"×18 gauge intubation needle. Animals were anaesthetized and surgically received an intrastriatal (right side only) injection of either 6-hydroxydopamine or saline. Animals were sacrificed one week after 6-hydroxy dopamine treatment.

Immediately following sacrifice, dissected striatal tissue was collected and analyzed by HPLC/EC for protein content using a bicinchoninic acid assay with the results shown in Table 5.

TABLE 5

Test side as percent of control side, only the right striatum having been injected with 6-Hydroxydopamine.

| Treatment | Percent of Control Side |
|---|---|
| Methyl Cellulose/6-hydroxydopamine | 69.67 ± 7.65 |
| 100 mg/kg CPI-1189/6-hydroxydopamine | 77.61 ± 13.5 |
| 50 mg/kg CPI-1189/6-hydroxydopamine | 72.82 ± 8.32 |

The results from these experiments show that CPI-1189 is able to protect against 6-hydroxydopamine induced dopamine depletion.

Alzheimer's Disease Activity Testing

Effect of Benzamides on Aβ(1-40) β-Pleated Sheets Formation: Detection of Amyloid Aggregation in Solution by Thioflavin T Fluorescence Spectra Several assays have been developed to assess the activity of compounds as agents for the treatment of Alzheimer's disease. One such assay draws on the observation that Alzheimer's patients exhibit unusual levels of amyloid aggregation.

Thioflavin T (ThT) rapidly associates with β pleated sheets particularly the aggregated fibrils of synthetic Aβ(1-40), giving rise to a new excitation maximum at 440 nm and enhanced emission at 490 nm. According to this principle, agents which could delay or reverse the formation of such association might be of therapeutic benefit.

Experiments were performed in 96 well plates and the fluorescence changes were evaluated using Fluorescence plate reader-CytoFluor II. Briefly, into each well was aliquoted 95 μl of ThT (3 μM) prepared in PBS (pH 6.0), 2 μl of NRT (10 μM) prepared in 0.05% of methylcellulose in PBS (pH 6.0), and 3 μl of Aβ(1-40)(3 μg) prepared with $dH_2O$. The fluorescence measurement began when Aβ(1-40) was added and continued for 4 hours at which the aggregation reached a plateau. The % protection of β-pleated sheet formation was calculated from the relative fluorescence unit difference between aggregation in the presence and in the absence of test compounds. The results are given in Table 6.

TABLE 6

Benzamide activity in Alzheimer's Screen

| Compound | % Protection |
|---|---|
| 1189 | 48.3 ± 10.1 |
| 1033 | 31.7 ± 3.5 |
| 1026 | 14.4 ± 14.4 |

Effect of Benzamides to Protect against the Amyloid β(25-35) or Glutamate-Induced Neuronal Cell Loss in Rat Embryonic Hippocampal Neuronal/Astrocytes Cultures Another Alzheimer's activity test was conducted. Sprague Dawley rat hippocampus of 18-day-gestation embryos was excised then dissociated by trituration to prepare primary neuronal/astrocyte cultures. Cells ($3 \times 10^5$) were plated on 35 mm poly-D-lysine-coated plates containing Eagle's minimum essential medium supplemented with 10% fetal bovine serum. After 3–5 hours, the original medium was removed and replaced with 1 ml of fresh medium. Cultures were maintained at 37° C. in a 5% $CO_2$/95% air humidified incubator.

For Aβ(25-35)-induced neuronal toxicity experiments: 30 μM of Aβ(25-35) dissolved in dH20 were added to the cells (7DIV) in the presence or absence of 100 μM benzamide prepared in 1% methylcellulose for 96 hours.

For glutamate-induced neuronal toxicity experiment: 30 μM of glutamate were added to the cells (9 DIV) in the presence or absence of benzamide for 48 hours.

Neuronal viability is expressed as the percentage of morphologically viable neurons after either 48 hours or 96 hours treatment to the number of neurons before treatment, in the same premarked culture regions (three regions/culture, n=6). Results are given in Table 7 with the data expressed as mean±SEM and compared with controls.

TABLE 7

Benzamide activity in Neuronal Cell Loss Screen

| Compound | % Protection $A_B(25-35)$ | % Protection Glutamate |
| --- | --- | --- |
| 1233 | 23 | |
| 1234 | 9 | |
| 1241 | 10 | |
| 1135 | 16 | |
| 1140 | 8 | 17 |
| 1146 | 50 | |
| 1173 | 36 | |
| 1240 | 23 | |
| 1026 | | 8 |

What is claimed is:

1. The compound N-tert-amyl-4-acetamidobenzamide.

2. The compound N-iso-propyl-4-acetamidobenzamide.

3. The compound N-methylcyclopropyl-4-acetamidobenzamide.

4. A pharmaceutical composition comprising a pharmaceutically inert carrier and a pharmaceutically effective amount of a compound of claim 1.

5. The pharmaceutical composition of claim 4 wherein the carrier is an oral carrier.

6. The pharmaceutical composition of claim 5 wherein said compound comprises 0.1 to 50 weight percent of said pharmaceutical composition.

7. The pharmaceutical composition of claim 6 wherein said compound comprises 1 to 40 weight percent of said pharmaceutical composition.

8. The pharmaceutical composition of claim 5 wherein said pharmaceutical composition is in a unit dosage form.

9. The pharmaceutical composition of claim 4 wherein the carrier is an injectable carrier.

10. The pharmaceutical composition of claim 9 wherein said compound comprises 0.05 to 10 weight percent of said pharmaceutical composition.

11. A pharmaceutical composition comprising a pharmaceutically inert carrier and a pharmaceutically effective amount of a compound of claim 2.

12. The pharmaceutical composition of claim 11 wherein the carrier is an oral carrier.

13. The pharmaceutical composition of claim 12 wherein said compound comprises 0.1 to 50 weight percent of said pharmaceutical composition.

14. The pharmaceutical composition of claim 13 wherein said compound comprises 1 to 40 weight percent of said pharmaceutical composition.

15. The pharmaceutical composition of claim 12 wherein said pharmaceutical composition is in a unit dosage form.

16. The pharmaceutical composition of claim 11 wherein the carrier is an injectable carrier.

17. The pharmaceutical composition of claim 16 wherein said compound comprises 0.05 to 10 weight percent of said pharmaceutical composition.

18. A pharmaceutical composition comprising a pharmaceutically inert carrier and a pharmaceutically effective amount of a compound of claim 3.

19. The pharmaceutical composition of claim 18 wherein the carrier is an oral carrier.

20. The pharmaceutical composition of claim 19 wherein said compound comprises 0.1 to 50 weight percent of said pharmaceutical composition.

21. The pharmaceutical composition of claim 20 wherein said compound comprises 1 to 40 weight percent of said pharmaceutical composition.

22. The pharmaceutical composition of claim 19 wherein said pharmaceutical composition is in a unit dosage form.

23. The pharmaceutical composition of claim 18 wherein the carrier is an injectable carrier.

24. The pharmaceutical composition of claim 23 wherein said compound comprises 0.05 to 10 weight percent of said pharmaceutical composition.

* * * * *